United States Patent [19]

Kamhi

[11] 4,449,050

[45] May 15, 1984

[54] DEVICE FOR PROCESSING PAPER MONEY

[76] Inventor: Ralph Kamhi, 261 W. 35th St., New York, N.Y. 10001

[21] Appl. No.: 361,749

[22] Filed: Mar. 25, 1982

[51] Int. Cl.³ .............................................. H01J 37/20
[52] U.S. Cl. .............................. 250/455.1; 134/122 R; 422/24
[58] Field of Search ................... 134/100, 64 R, 64 P, 134/122 R, 122 P; 15/77; 422/24; 250/455.1

[56] References Cited

U.S. PATENT DOCUMENTS

| | | | |
|---|---|---|---|
| 3,492,933 | 2/1970 | Knibiehly et al. | 134/122 P |
| 3,922,702 | 11/1975 | Gaskell | 134/122 P X |
| 4,001,838 | 1/1977 | Maddox | 134/122 R X |
| 4,327,456 | 5/1982 | Deconinck | 134/122 P X |

FOREIGN PATENT DOCUMENTS 2711621  9/1978  Fed. Rep. of Germany ........ 422/24

*Primary Examiner*—Stephen Marcus
*Assistant Examiner*—Renee S. Kidorf
*Attorney, Agent, or Firm*—Bauer & Amer

[57] ABSTRACT

A compact-sized device for feeding a lengthwise oriented U.S. dollar bill, or the like, in a C-shaped feed path about a centrally located ultraviolet source, which contributes to the sterilizing of the bill. Cooperating pairs of rollers in corner locations in relation to chutes maintain proper feed control over the bill wherein the spacing of the rollers is selected so that either a leading or a trailing edge of the bill is engaged in the bight of a pair of rollers at all times, thereby subjecting the bill to a positive feed action.

1 Claim, 6 Drawing Figures

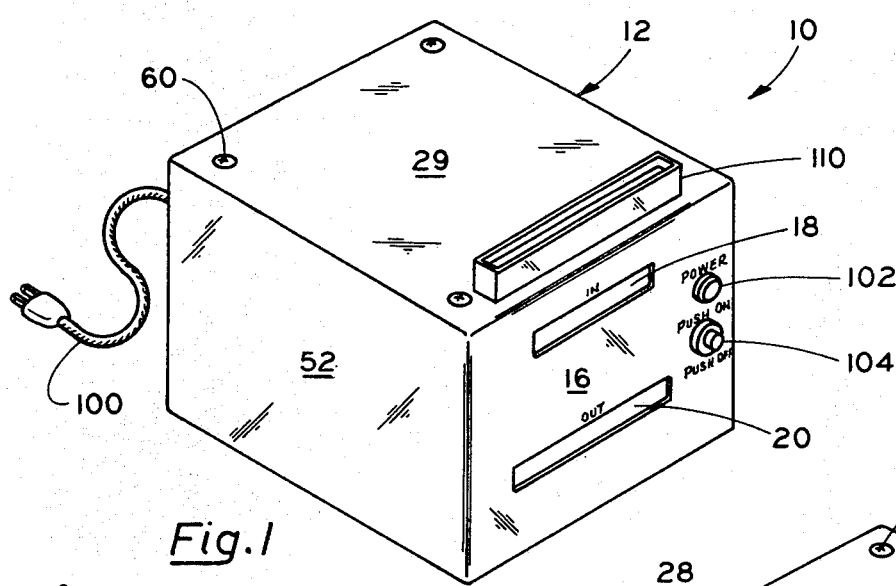
Fig.1
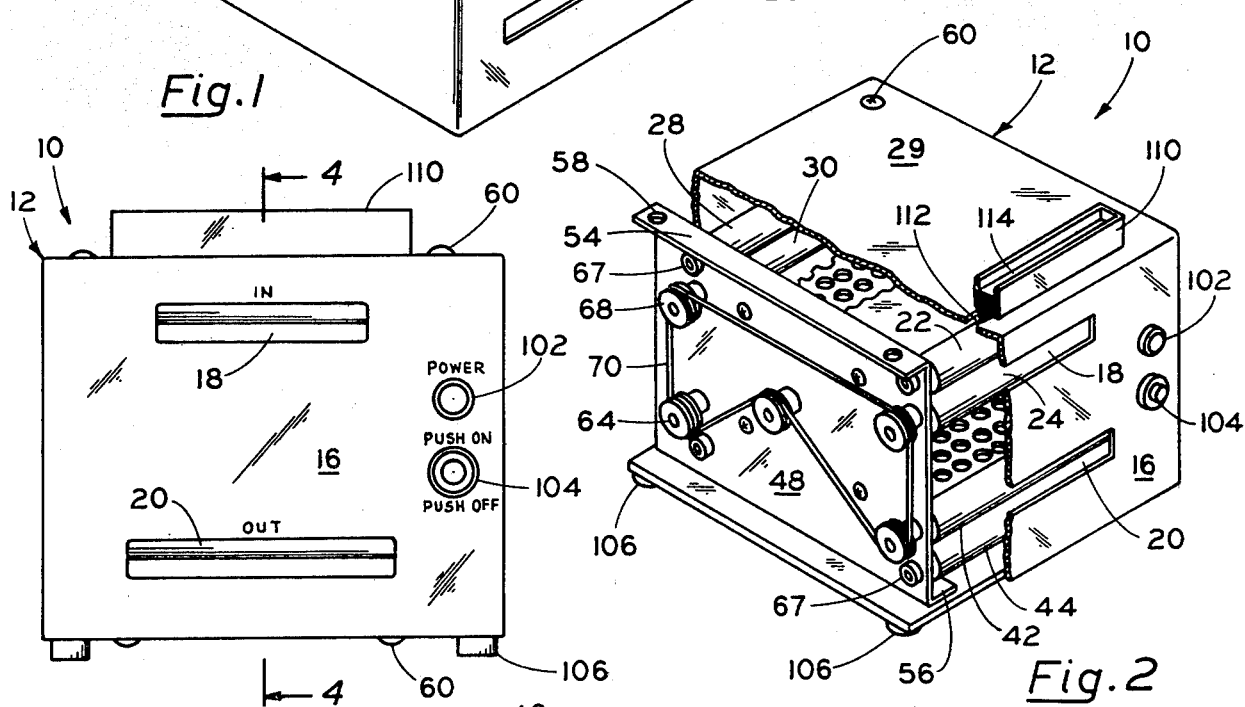
Fig.2
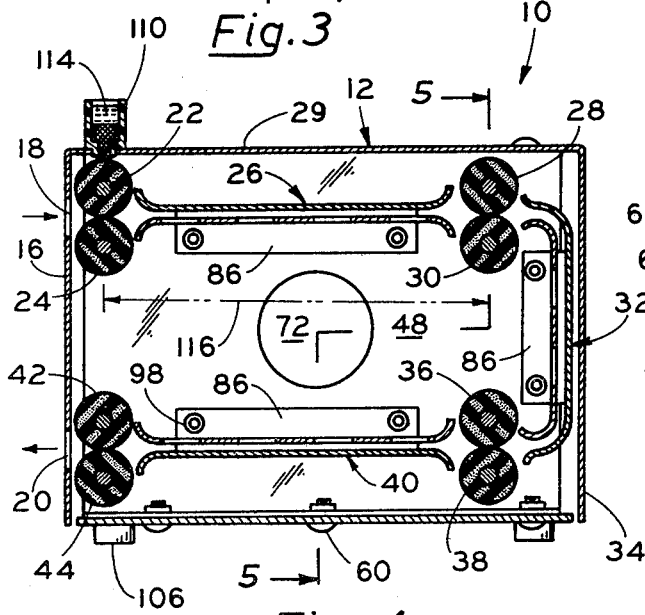
Fig.3
Fig.4
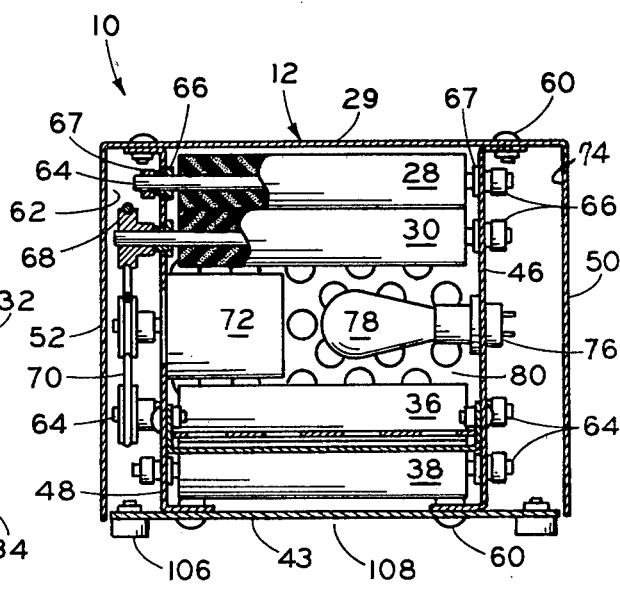
Fig.5

DEVICE FOR PROCESSING PAPER MONEY

The present invention relates generally to a sterilization device for paper currency, and more particularly to an improved device for urging a dollar bill or the like in cleansing relation to an ultraviolet source.

It is already well known, as exemplified by laundry finishing equipment, that sterilization of clothing can be achieved by ultraviolet irradiation. There are also numerous examples of ultraviolet sterilization of barbers' implements, toothbrushes, or the like. These known devices, however, have not been effectively embodied in a compact size, appropriate for use at a cash register or other check-out location, such that this sterilizing technique can be used for paper currency, a major source of germ and disease transmission.

Broadly, it is an object of the present invention to provide an ultraviolet sterilizing device specifically for dollar bills or the like, wherein such currency-processing device overcomes the foregoing shortcomings in size and compactness of the prior art. More specifically, it is an object to provide a device suitable for use at a check-out location for a restaurant or the like, in the operation of which a currency bill is effectively cleansed or sterilized by ultraviolet lamps.

In a currency-sterilizing device demonstrating objects and advantages of the present invention, use is made of a rectangular, compact-sized compartment including three chute means each respectively mounted in a clearance position internally of the top, bottom and rear of said compartment, so as to define a C-shaped feed path. Cooperating with these chutes are four motor-driven pairs of cooperating rollers operatively located in interposed positions between each adjacent two chutes so that the combined operative effect of the chutes and the rollers is to urge paper money from an input slot into the device through movement along the C-shaped curved path of the three chutes and out through an output slot. Of significance are the operative locations of the four pairs of rollers, the same being selected with respect to each other so as to be less than the length of the paper money, whereby a unit of paper money fed lengthwise into the input slot is always in engagement at either a leading or trailing edge thereof with one of the pairs of rollers during movement through the device, to thereby contribute to a positive feed thereof which obviates any internal jamming.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIG. 1 is a perspective view of a paper money-processing device intended principally for U.S. currency. Thus, although appearing larger in FIG. 1, it will be understood to be only approximately 10 inches by 8 inches by 10 inches;

FIG. 2, like FIG. 1, is similarly a perspective view, but with the left side portion removed to better illustrate internal structural features;

FIG. 3 is a front elevational view illustrating the input and output slots for the paper money being fed into and exiting from the device;

FIG. 4 is a side elevational view, taken in section along line 4—4 of FIG. 3, illustrating details of the pairs of rollers used internally of the device to urge the paper money along its prescribed path;

FIG. 5 is also a sectioned side elevational view, but taken along line 5—5 of FIG. 4, and illustrating additional features, particularly those of the drive for the rollers.

Figure 6:
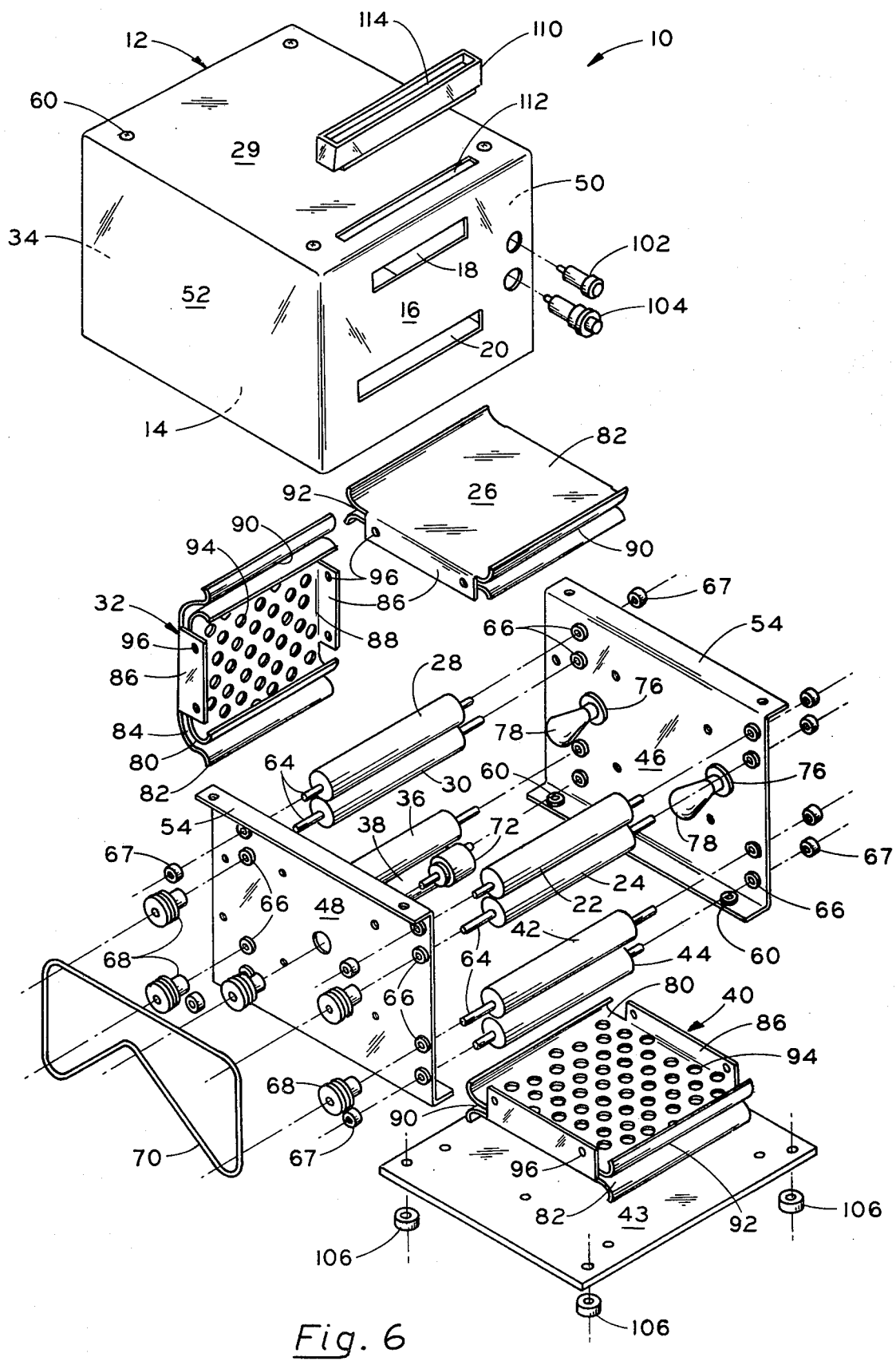
FIG. 6 is an exploded, perspective view of the various components which comprise the within inventive device.

The paper money-processing device demonstrating objects and advantages of the present invention is generally designated 10, and is shown in assembled condition in FIG. 1 and in disassembled condition in FIG. 6. By a comparison of FIGS. 1 and 6, it should be readily noted that device 10 includes an external housing 12 which bounds a rectangular compartment 14 for the various operative components soon to be described in detail. Before such detailed description, however, it is helpful to generally note these components, and also their operative relation to each other.

Still referring to FIGS. 1 and 6, it will be noted that in a front panel 16 of housing 12 there is an input slot 18 and an output slot 20, through which, as the names imply, the paper money is initially inserted into the device and subsequently exits therefrom.

As will be better understood as the description proceeds, but which nevertheless can be readily surmised from FIG. 6, there is located internally of the housing 12 in the path of insertion through the inlet slot 18, a first-encountered pair of rollers designated 22 and 24, which will be understood to be of electromeric construction material, and which are effective to engage the paper money being inserted into the bight of the rollers.

Rotation of the rollers 22 and 24 will be understood to be in a direction which then urges the paper money through a first-encountered chute 26 which is appropriately mounted, internally of the housing 12 in a clearance position beneath the upper panel 28 thereof.

The paper money exits from the chute 26 and is then engaged by a second-encountered pair of rollers 28 and 30, which are similar in major respects to the previously noted rollers 22 and 24, except, of course, that these rollers are located at the exit end of the chute 26.

It will be understood that the paper money engaged between the rollers 28, 30, is urged by their rotative movement into a second-encountered chute 32. Chute 32 is operatively mounted in a clearance position within the housing 12 in front of the rear panel 34 thereof.

Exiting from the chute 32, the paper money is engaged by a third-encountered pair of rollers 36 and 38, which rollers are effective to change the path of movement of the paper money approximately 90 degrees and to urge said paper money into a third-and last-encountered chute 40. Chute 40 is appropriately mounted slightly above the housing bottom panel 43 and is effective in directing the paper money being fed through the device 10 to a fourth- or last-encountered pair of rollers 42,44. The paper money, such as a U.S. dollar bill or the like, is expelled out of the bight of the rollers 42,44 and out of the output slot 20 of the device 10, it being understood that the rollers 42,44 are in an appropriate aligned adjacent position to the output slot 20.

To achieve positioning of the four pairs of rollers with the three chutes as just noted, use is advantageously made of two mounting plates or brackets 46 and 48 which are appropriately stationarily positioned within the housing 12 in a prescribed clearance position from each of the housing sides 50 and 52, respectively. Using bracket 48 as illustrative of the mounting of both brackets, reference should be made to FIG. 2 in which it will be noted that bracket 48 has laterally extending flanges 54 and 56 with appropriate bolt openings 58 which in a well understood manner, and as illustrated for example in FIG. 5, readily permit the bracket 48 to be connected by bolt and nut means 60 in a vertically oriented condition between the housing top and bottom panels 29 and 43.

Still referring to FIG. 5, it will be noted that the clearance between the bracket 48 and housing side 52 adjacent thereto, is effective to bound or provide a compartment 62 for the drive of the cooperating pairs of rollers 22-44, previously noted. That is, and as may be best appreciated by progressive examination of FIGS. 2 and 5, the shifts, individually and collectively designated 64, of the lower roller of the upper pairs and the upper roller of the lower pairs, and thus constituting the shafts which are closest to each other, are extended through bearings, individually and collectively designated 66, into said compartment 62. One each of the projecting ends of the shafts 64 within the compartment 62, there is then appropriately mounted on each a pulley 68 on which there is appropriately entrained a pulley belt 70. Completing the drive connection is an electric motor 72 mounted to extend through a central opening 73 of bracket 48 and thus also into the left-hand side compartment 62. On the shaft of the motor 72 there is also mounted a pulley 68 operatively arranged to transmit the drive of the motor via the closed loop of the pulley belt 70 to the rollers 24, 30, 36 and 42. In this manner, the cooperating pairs of rollers mounted at the four corner locations previously noted are each driven in rotation at a uniform speed by the motor 72.

With respect to the other mounting bracket 46, reference should now be made to FIG. 5 which illustrates that this bracket is also mounted in a clearance position from the housing side panel 50 adjacent thereto and thus also provides a side compartment 74. Compartment 74 is used not only for receiving the opposite ends of the shaft mounting the rollers and, more particularly the collars and bushings or bearings 66 thereof, but it also more importantly serves as a compartment for the electrical connection 76 for ultraviolet lamps 78 that are mounted to extend from the bracket 46, as best illustrated in FIG. 6 in conjunction with FIG. 5, into a central compartment 80 of the housing 12 which exists as a result of the open space between the corner-located previously noted cooperating pairs of rollers. As a result, and although not shown in FIG. 5, it should be readily understood that an electrical connection from an appropriate electrical source, such as an outlet or the like, can be made through a wire conductor to the connection 76 and thus energize the lamps 78 so that they are an effective source of a light emission in the ultraviolet frequency. This emission, also as is well understood, is known to have an antiseptic effect on materials upon which it impinges. Thus, paper dollar bills fed through the device 10 and exposed to the ultraviolet emission of the lamps 78 are effectively sterilized and placed in a more desirable and optimum condition for handling and use.

For completeness sake, some description is required of the construction and mounting of the three encountered chutes 26, 32 and 40, although it is believed that such construction and mounting can readily be understood from the disassembled view of FIG. 6 and the assembled and sectioned views of FIGS. 2, 4 and 5. Taking chute 32, however, as exemplary of the other two chutes 26 and 42, and having specific reference to FIGS. 6 and 4, it will be noted that chute 32 is comprised of two spaced-apart plates 80 and 82, preferably of metal, wherein the spacing therebetween bounds a passageway 84. The plates 80, 82 are advantageously held in spaced-apart relation by a pair of flanges 86 which extend from the plate 82 and are bent transversely thereof, and as such, effectively serve as structural features to which the other plate 80 is appropriately attached, as by welding, as at 88. At opposite ends, plates 80 and 82 are bent in an outwardly diverging relation from each other so as to constitute an appropriate shape for an inlet 90 and an outlet 92, thus facilitating movement into and out of the chute 32.

To achieve impingement of the ultraviolet emission from the lamps 78 on the paper money during its movement through the chute 32, the inner plate 80 is appropriately provided throughout its extent with numerous openings, individually and collectively designated 94. Using bolt holes 96 in the flanges 86, chute 32, as best illustrated in FIG. 4, is readily mounted by bolt and nut means 98 in its operative position supported at opposite ends by the mounting brackets 46 and 48. In like manner, and having the structural features already described in connection with chute 32 and designated by the same reference numerals in connection with the other chutes 26 and 40, all of the three chutes are effectively mounted with respect to the cooperating pairs of rollers in their operative positions as illustrated between the mounting brackets 46 and 48.

The device 10 will, of course, be understood to be completed with conventional components that will facilitate its use. For example, and as should be well understood, the device 10 will include, as illustrated in FIG. 1, an electric cord connection 100 for energizing the ultraviolet lamps 78, an on-and-off push button 104 and light signal 102 for operating the lamps. Also, since it is contemplated that device 10 will be at a cash register of a restaurant or other such establishment, the commercial embodiment will include rubber pads 106 at the four corners of the bottom plate 42 to prevent damage to the support surface and also to provide the necessary clearance 108 for the bolt heads 60 used in the internal mounting of the brackets 46 and 48.

A preferred embodiment of the device 10 herein will also include a cleaning fluid trough 110 mounted in appropriately sized slot 112 in the top panel 28 so as to effectively meter the antiseptic fluid 114 through a bottom opening and onto the upper roller 22 of the first-encountered pair of rollers, all as illustrated in FIG. 4. It is contemplated that the dispensed fluid will assist the ultraviolet emission in sterilizing the paper money.

Referring to FIG. 4, it will be noted that in accordance with the present invention the relative locations of the cooperating pairs of rollers are intentionally selected so as to be less than the 6 inch length of a U.S. dollar bill. That is, the distances denoted by the reference arrow 116 between the first-encountered pair of rollers 22, 24, and the second-encountered pair of rollers 28, 30 (and thus also for the distance between the third-and fourth-encountered pairs of rollers) is less than 6 inches, being, in a preferred embodiment only 5 inches. The reason for this is that it is desired that the U.S. dollar bill, which is fed lengthwise into the device 10, always be in engagement at either a leading or trailing edge thereof with a pair of rollers. This, of course, is achieved since the leading edge of the dollar bill is engaged in the bight of the rollers 28, 30, while the trailing edge thereof is just exiting from the bight of the first-encountered pair of rollers 22, 24. The distance, of course, between the second- and third-encountered pair of rollers is considerably less than the length of the dollar bill, such that the operating parameter that the dollar bill always being in engagement with a driving pair of rollers is readily achieved during movement of the dollar bill through the chute 32.

From the foregoing, it should be readily appreciated that there has been described herein a compact-sized device which is readily adapted to process paper money in cleansing relation past an ultraviolet source causing the sterilization of the paper money. Device 10 is accordingly of utilitarian use at check-out counters or cash registers for restaurants or other such establishments which, with regard to both employees and customers, and thus with respect to individuals who handle both food and currency, provides assurance that such activity occurs under optimum sterile conditions.

A latitude of modification, change and substitution is intended in the foregoing description, and in some instances, some features of the invention will be employed without a corresponding use of other features. Accordingly, it is appropriate that the appended claims be construed broadly and in a manner consistent with the spirit and scope of the invention herein.

What is claimed is:

1. A device for urging paper money of an elongated rectangular size of a prescribed length and width through movement in cleansing relation to an ultraviolet lamp source comprising a housing having a front panel, opposing top and bottom panels, a rear panel, and opposite side panels, an input slot and an output slot in said front panel for said paper money, three chute means each respectively mounted in a clearance position internally of said top, bottom and said rear panels and in spanning relation between said opposite side panels so as to bound a central compartment for an ultraviolet lamp source and also defining a curved path for said paper money through said chutes, four motor-driven pairs of cooperating rollers operatively located in spanning relation between said opposite sides with two such pairs in interposed positions between said input and output slots and the ends of said two chutes adjacent thereto and with said other two such pairs in positions adjacent the other ends of said two pairs in positions adjacent the other ends of said two chutes and at the opposite ends of said third chute to thereby urge said paper money from said input slot through movement along said curved path of said three chutes and out through said output slot, each lower roller of the upper pairs of rollers and each upper roller of the lower pairs of rollers being mounted on shafts which extend beyond one said housing side panel, a pulley means and means connected therefrom to said shafts for completing an operative driving connection made by said pulley means to said shafts for driving said pairs of rollers at a selected uniform speed, said operative locations of said four pairs of rollers being selected with respect to each other so as to be less than the length of said paper money, whereby a unit of paper money fed lengthwise into said input slot is always in engagement at either a leading or trailing edge thereof with one of said pairs of rollers during movement through said device to thereby contribute to the positive feed thereof so as to obviate any internal jamming, and an ultraviolet light source mounted to extend into said central compartment from said other housing side panel, whereby the motor drive for said rollers and the energizing connection to said ultraviolet light source are on opposite sides of said device to thereby contribute an optimum compact size therein.

* * * * *